US010139337B2

(12) United States Patent
Greegor et al.

(10) Patent No.: US 10,139,337 B2
(45) Date of Patent: Nov. 27, 2018

(54) SYSTEM AND METHOD FOR TESTING A MATERIAL SYSTEM

(71) Applicant: The Boeing Company, Chicago, IL (US)

(72) Inventors: Robert B. Greegor, Black Diamond, WA (US); Jeffrey D. Morgan, Auburn, WA (US); Quynhgiao N. Le, Bellevue, WA (US); Julie M. Drexler, Brier, WA (US); John A. Mittleider, Kent, WA (US)

(73) Assignee: The Boeing Company, Chicago, IL (US)

( * ) Notice: Subject to any disclaimer, the term of this patent is extended or adjusted under 35 U.S.C. 154(b) by 38 days.

(21) Appl. No.: 14/174,550

(22) Filed: Feb. 6, 2014

(65) Prior Publication Data

US 2015/0219551 A1    Aug. 6, 2015

(51) Int. Cl.
| | |
|---|---|
| *G01N 3/32* | (2006.01) |
| *G01N 19/08* | (2006.01) |
| *G01M 5/00* | (2006.01) |
| *B06B 3/00* | (2006.01) |

(52) U.S. Cl.
CPC .............. *G01N 19/08* (2013.01); *B06B 3/00* (2013.01); *G01M 5/005* (2013.01); *G01M 5/0083* (2013.01); *G01M 5/0091* (2013.01); *G01N 3/32* (2013.01); *G01N 2203/0005* (2013.01); *G01N 2203/0069* (2013.01); *G01N 2203/022* (2013.01); *G01N 2203/0236* (2013.01); *G01N 2203/0282* (2013.01)

(58) Field of Classification Search
CPC .... G01N 19/08; G01N 3/32; G01N 2203/005; G01M 7/06

USPC .......................................... 73/808, 810, 856
See application file for complete search history.

(56) References Cited

U.S. PATENT DOCUMENTS

| | | | |
|---|---|---|---|
| 3,665,751 A | 5/1972 | Demogenes et al. | |
| 5,188,456 A * | 2/1993 | Burke | G01N 3/08 374/50 |

(Continued)

FOREIGN PATENT DOCUMENTS

| | | |
|---|---|---|
| JP | 2002-22630 A | 1/2002 |
| WO | WO 03/019150 | 3/2003 |
| WO | WO 2010/003154 A1 | 7/2010 |

OTHER PUBLICATIONS

Authors: Sung Ryul Choi, John W. Hutchinson, A.G. Evans, Title: Delamination of multilayer thermal barrier coatings, Date: 1999, Publication: Mechanics of Materials, Edition 31 , pp. 431-447.*

(Continued)

*Primary Examiner* — Lisa Caputo
*Assistant Examiner* — Roger Hernandez-Prewit
(74) *Attorney, Agent, or Firm* — Walters & Wasylyna LLC

(57) ABSTRACT

A system and method for testing a material system may include a support structure for mounting the material system, and a electromechanical device operably connected to the support structure, wherein the electromechanical device applies an electromechanical-induced force to the material system, and wherein the electromechanical-induced force causes a displacement in the material system equivalent to material displacement from thermal stress in significantly less time.

21 Claims, 12 Drawing Sheets

(56) References Cited

U.S. PATENT DOCUMENTS

| | | | | |
|---|---|---|---|---|
| 5,424,634 A * | 6/1995 | Goldfarb | G01N 3/36 | |
| | | | 324/763.01 | |
| 5,621,243 A * | 4/1997 | Baba | H01L 23/3735 | |
| | | | 257/712 | |
| 5,838,568 A * | 11/1998 | Dickinson et al. | G01R 31/30 | |
| | | | 700/121 | |
| 5,945,607 A * | 8/1999 | Peppel | G01N 3/04 | |
| | | | 73/831 | |
| 6,023,985 A * | 2/2000 | Fournier | G01N 33/0016 | |
| | | | 73/865.6 | |
| 6,035,715 A * | 3/2000 | Porter | G01M 7/02 | |
| | | | 73/432.1 | |
| 6,050,138 A | 4/2000 | Lynch et al. | | |
| 6,058,784 A * | 5/2000 | Carroll | G01N 3/10 | |
| | | | 73/831 | |
| 6,247,366 B1 * | 6/2001 | Porter | G01M 7/02 | |
| | | | 73/432.1 | |
| 6,664,067 B1 | 12/2003 | Hadjuk et al. | | |
| 7,745,972 B2 * | 6/2010 | Otaguro | H02N 2/028 | |
| | | | 310/323.17 | |
| 8,474,324 B2 | 7/2013 | Rihan et al. | | |
| 2002/0017144 A1 * | 2/2002 | Miles et al. | G01N 3/32 | |
| | | | 73/808 | |
| 2002/0023507 A1 | 2/2002 | Hajduk et al. | | |
| 2009/0151989 A1 * | 6/2009 | Hunrath | H05K 1/0271 | |
| | | | 174/257 | |
| 2010/0036636 A1 | 2/2010 | Oh et al. | | |
| 2011/0239771 A1 * | 10/2011 | Wu | G01M 7/06 | |
| | | | 73/663 | |
| 2012/0012553 A1 * | 1/2012 | Japp et al. | B32B 37/02 | |
| | | | 216/18 | |
| 2012/0240687 A1 * | 9/2012 | Miyakozawa et al. | G01N 3/04 | |
| | | | 73/808 | |
| 2013/0340511 A1 | 12/2013 | Miller et al. | | |
| 2014/0276230 A1 * | 9/2014 | Pattison | G06F 19/3437 | |
| | | | 600/587 | |

OTHER PUBLICATIONS

Author: Christopher C. Berndt, Title: Material Property Measurements on Thermal Barrier Coatings, Date: 1988, Publisher: The American Society of Mechanical Engineers, pp. 6 total.*

Author: M. Bartsch, B. Baufeld, M. Henzelmann, Anette M. Karlsson and S. Dalkilic, Title: Multiaxial Thermo-Mechanical Fatigue on Material Systems for Gas Turbines, Date: Sep. 2007, Publisher: Cleveland State University, Mechanical Engineering Department, pp. 10 total.*

Author: Unknown, Title: XYZ Piezo Positioning Flexure Stages, Nanometer and Picometer Resolution, High Speed & Stability, Date: Jun. 2011, Publisher: Physik Instrumente (PI), pp. 21.*

Canadian Intellectual Property Office, Examination Report, CA 2,875,709 (dated Dec. 16, 2015). pp. 4.

European Patent Office, Communication Pursuant to Article 94(3) EPC, 14 198 668.7, (dated Mar. 3, 2017), 8 pages total.

Innovation, Science and Economic Development Canada, (Nov. 27, 2017), Application #: 2,875,709.

Canadian Intellectual Property Office, "Examination Search Report," App. No. 2,875,709 (dated Aug. 15, 2018), 5 pages.

Japanese Patent Office, "Examination Report," with English Translation, App. No. 2015-008406 (dated Jun. 15, 2018), 8 pages.

The State Intellectual Property Office of China, "First Notification of Office Action," with English translation, App. No. 201510028585.2 (dated Jun. 26, 2018), 13 pages.

* cited by examiner

SYSTEM AND METHOD FOR TESTING A MATERIAL SYSTEM

FIELD

The present disclosure is generally related to material testing and, more particularly, to a system and method for testing a material system employing mechanical displacement cycling as a replacement for materials effects assessment from thermal cycling.

BACKGROUND

Cracking of surface materials and other finish systems, such as coatings, applique and/or fastener interfaces, may develop on a variety of structures as the result of environmental stress. Cracks occurring in the finish system may propagate to the underlying structure providing a path for moisture and other environmental species to enter, resulting in corrosion and degradation of the functionality of the finish system and the structures being protected by the finish system.

In many applications, the durability of a material system (e.g., an underlying structure and a finish system) must be tested in order to insure that the finish system can withstand the environment to which it will be subjected. Material system testing may include the process of subjecting the underlying structure and/or any finish systems to thermal cycling (e.g., cycling through two temperature extremes, typically at relatively high rates of change). The material system may be temperature cycled to insure that crack formation does not occur over the desired lifetime of the finish system due to a mismatch in coefficients of thermal expansion of the different material systems or other changes in physical properties.

For example, in the aerospace industry, finish systems (e.g., protective coatings and/or fastener interfaces) for aluminum and/or composite structures must be qualified to determine their efficacy in protecting the underlying structure (e.g., an aircraft) from deleterious environmental exposure in service over the lifetime of the material system and/or the finish system. Thermal cycling testing, designed to simulate the environmental stress experienced over the lifetime of the design, may be both time-consuming and expensive. Thus, it may be problematic to screen a large number of potential material system candidates having different material parameters for the finish system.

Additionally, material system candidates may be tested using environmental chambers that replicate the humidity and temperatures that the underlying structure and the finish system would experience. Operation of environmental chambers to screen for the efficacy of potential finish system may further increase cost and time.

For example, thermal screening of the material system may take months to accomplish before a finish system is fully characterized. This may be due, in part, to the multi-layered nature of many finish systems and the large number of parameters that need to be optimized and taken into account. After a material system candidate has been developed, a single thermal cycle (e.g., a cycle sufficient to cause the finish system to expand and contract) may take many hours. Numerous thermal cycles may constitute a testing block (e.g., 1 testing block=400 thermal cycles). Numerous testing blocks may need to be repeated to adequately simulate a typical service life of the material system candidate (e.g., the design of the underlying structure and/or the finish system) and/or before cracks appear.

Therefore, screening of just one potential finish system candidate may be tedious, time consuming and expensive using conventional testing solutions.

Accordingly, those skilled in the art continue with research and development efforts in the field of material testing and, in particular, testing for cracks in surface finish systems.

SUMMARY

In one embodiment, the disclosed system for testing a material system may include a support structure for mounting the material system, and an electromechanical device operably connected to the support structure, wherein the electromechanical device applies an electromechanical-induced force to the material system, and wherein the electromechanical-induced force causes a displacement in the material system, wherein the electromechanical-induced force is calibrated to be equivalent to a displacement that would be caused by thermal stress.

In another embodiment, disclosed is a method for testing a material system, the method may include the steps of: (1) mounting the material system to a support structure, (2) applying an electromechanical-induced force to the material system, wherein the electromechanical-induced force causes a displacement in the material system, and (3) maintaining the electromechanical-induced force.

Other embodiments of the disclosed system and method for testing a material system will become apparent from the following detailed description, the accompanying drawings and the appended claims.

DETAILED DESCRIPTION

Figure 1:
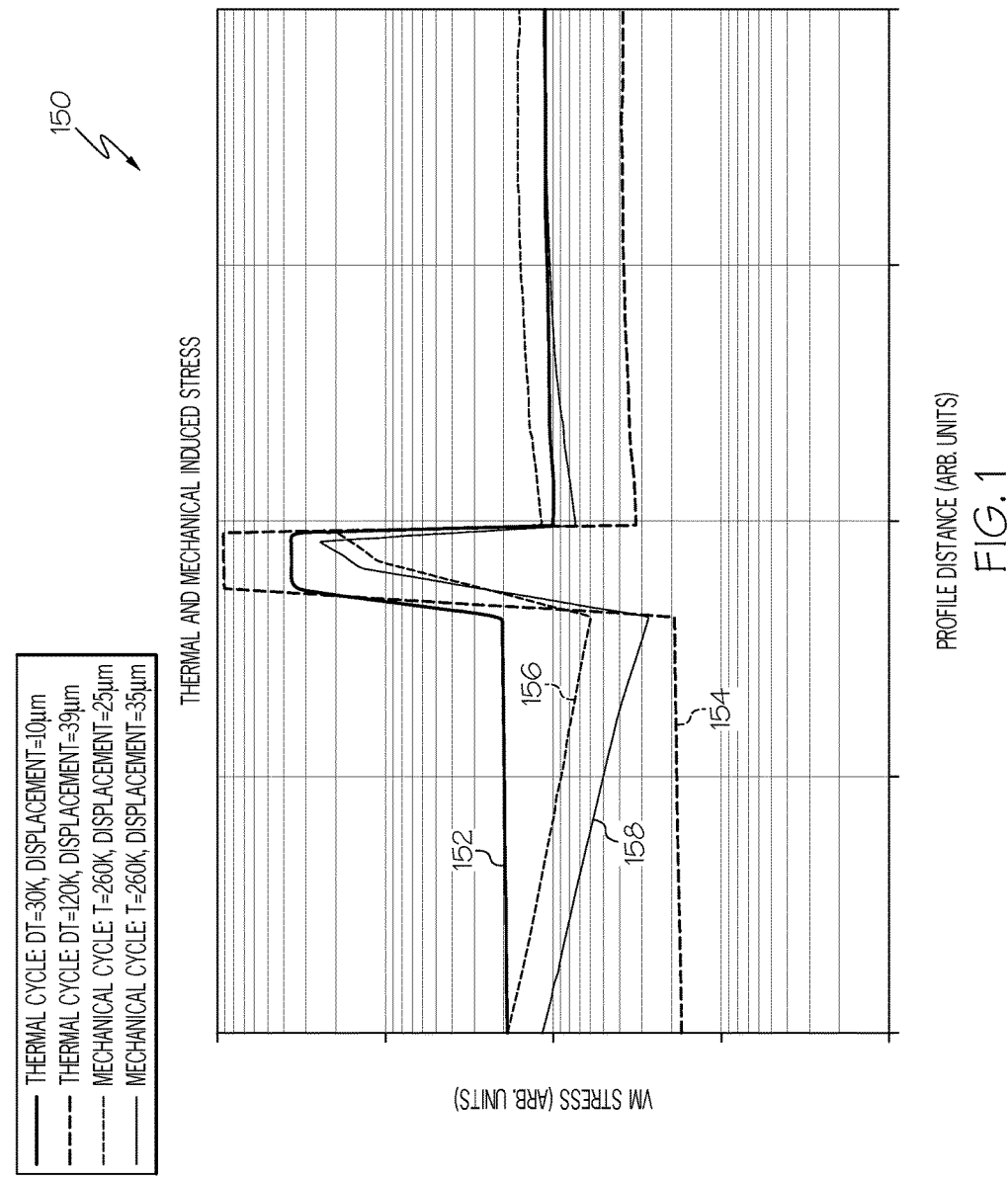
FIG. 1 is an illustration of an example graph of thermal induced stresses and mechanical induced stresses throughout a profile of a material system.

The following detailed description refers to the accompanying drawings, which illustrate specific embodiments of the disclosure. Other embodiments having different structures and operations do not depart from the scope of the present disclosure. Like reference numerals may refer to the same element or component in the different drawings.

The present disclosure recognizes and takes into account that thermal cycling of a material system has been demonstrated to result in differential expansion (e.g., thermal displacement) that introduces stresses to the material system. For example, thermal cycling may cause an "up and down" motion of the material system (e.g., at a surface interface or at a perimeter of a fastener). This motion effect caused by thermal displacement may be roughly equivalent to a motion effect from mechanical displacements that may be replicated mechanically. Accordingly, a mechanical cycle of the material system has been demonstrated to result in mechanical displacement of the material system that produces stresses that are substantially equivalent to stresses introduced to the material system due to thermal displacement.

FIG. 1 illustrates an example graph 150 of Von Mises ("VM") stress throughout a profile (e.g., thickness) of a material system in response to thermal displacements (e.g., resulting from thermal cycling) and substantially equivalent mechanical displacements (e.g., resulting from mechanical cycling). The example graph 150 illustrates the VM stress and profile distance in arbitrary units (ARB. Units).

For example, line 152 may represent the VM stress throughout the profile of an example material system subjected to a thermal cycle having a temperature change ("DT") of approximately 30K and a thermal displacement of approximately 10 microns (um). Line 154 may represent the VM stress throughout the profile of the example material system subjected to a thermal cycle having a temperature change of approximately 120K and a thermal displacement of approximately 39 microns. Line 156 may represent the VM stress throughout the profile of the example material system subjected to a mechanical cycle having a temperature ("T") of approximately 260K and a mechanical displacement of approximately 25 microns. Line 158 may represent the VM stress throughout the profile of the example material system subjected to a mechanical cycle having a temperature of approximately 260K and a mechanical displacement of approximately 35 microns.

Figure 2:
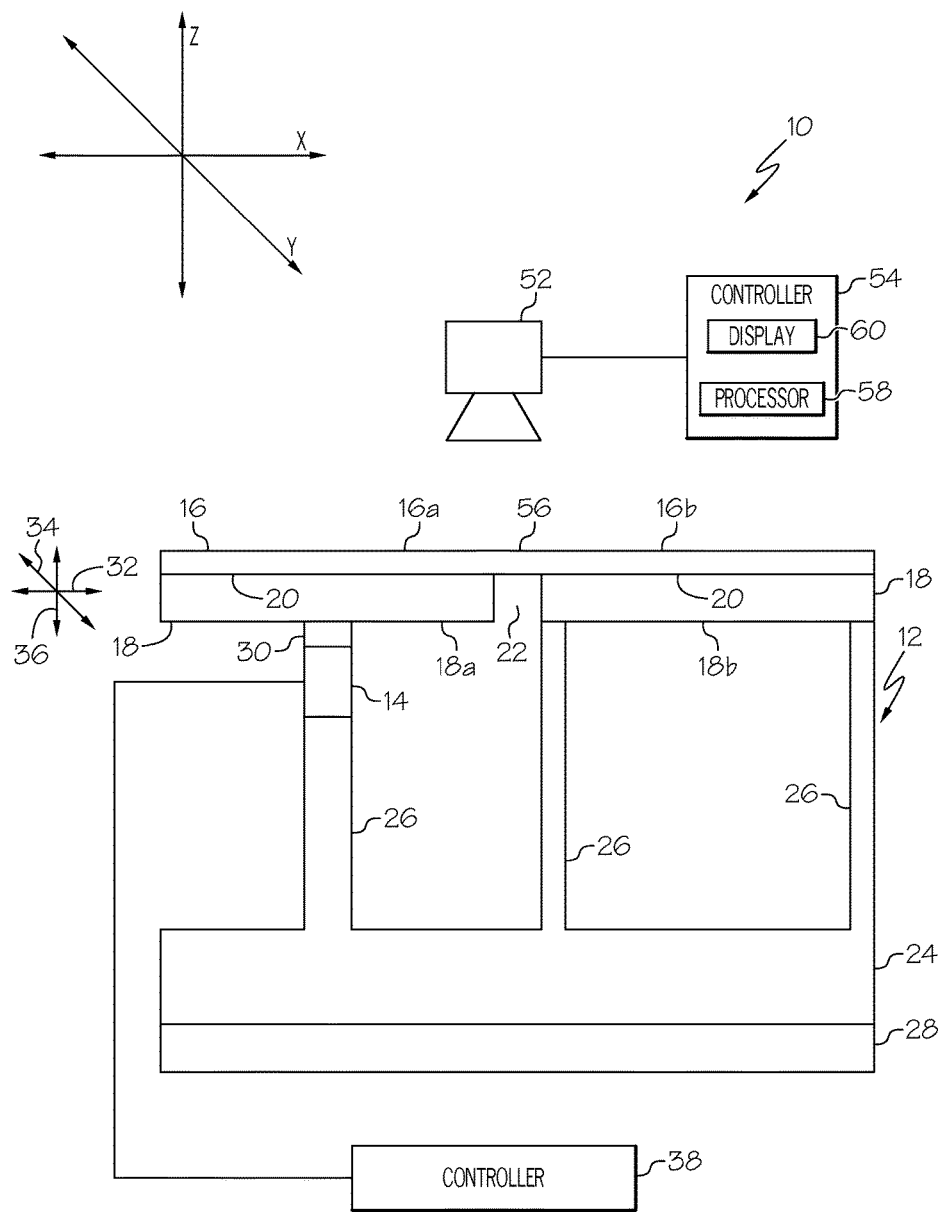
FIG. 2 is a schematic illustration of one embodiment of the disclosed system for testing a material system.
Figure 3:
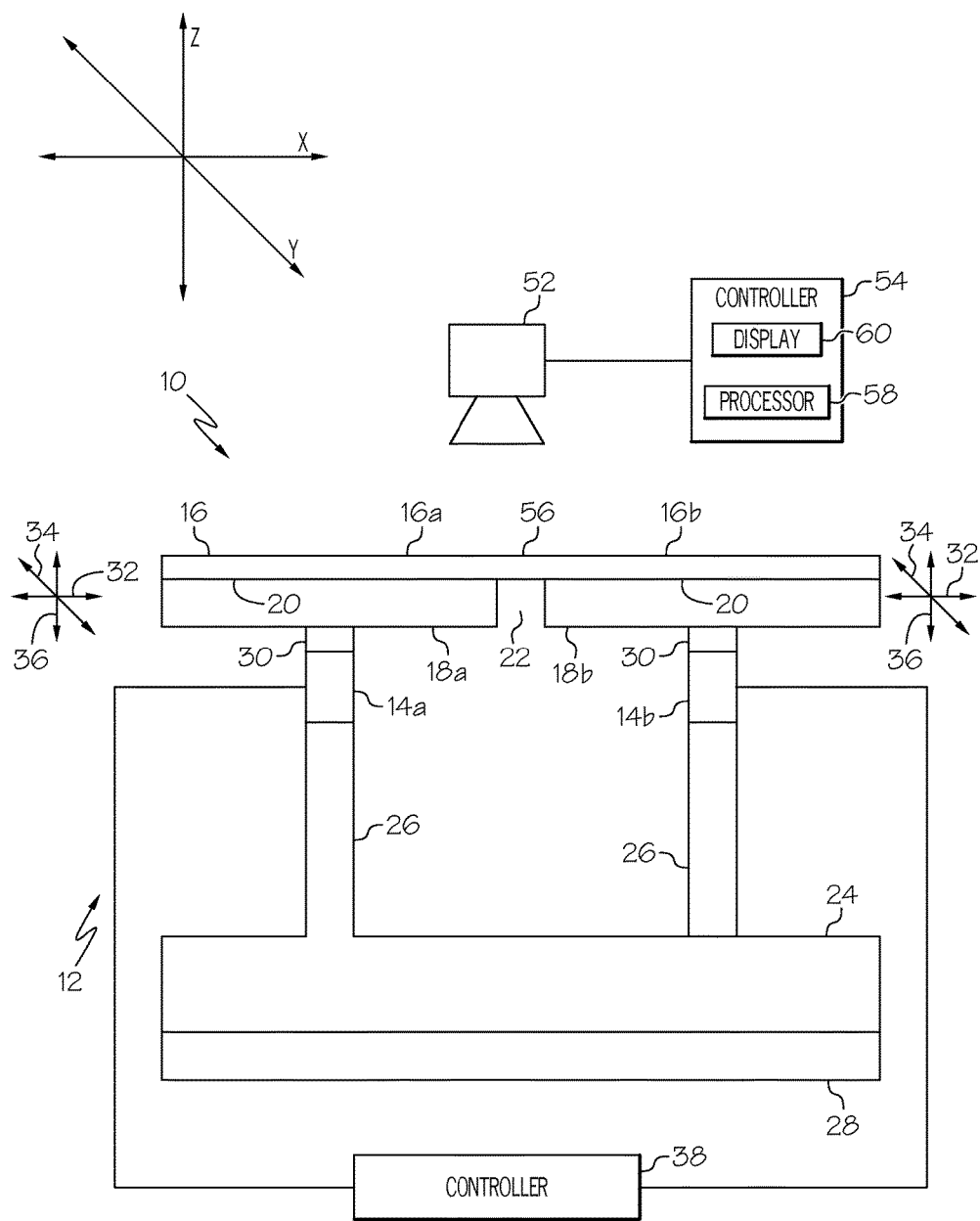
FIG. 3 is a schematic illustration of another embodiment of the disclosed system.
Figure 4:
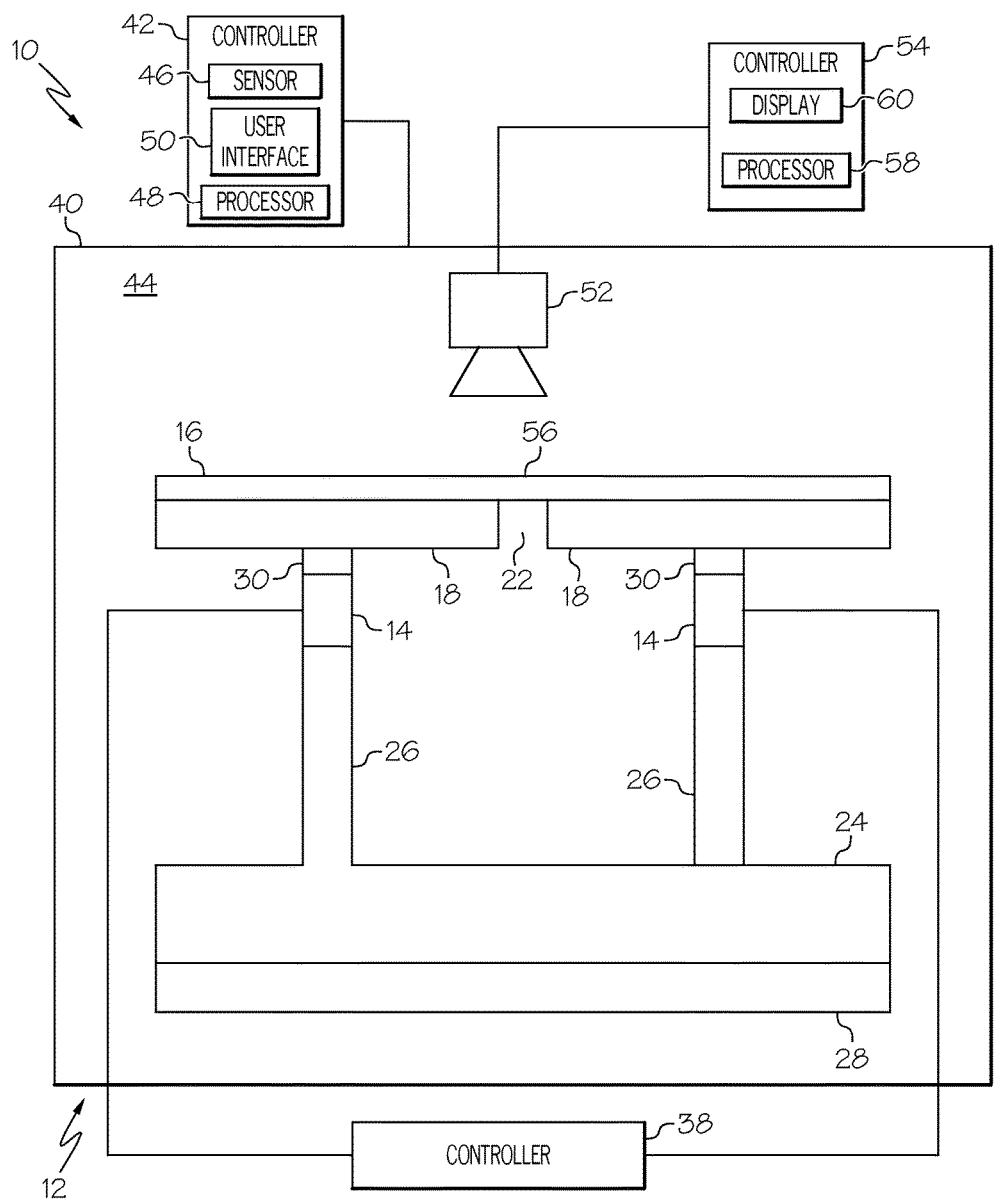
FIG. 4 is a schematic illustration of another embodiment of the disclosed system.

Referring to FIGS. 2-4, the disclosed system, generally designated 10, for testing a material system may include a support structure 12 and one or more electromechanical devices 14 operably connected to the support structure 12. Throughout the present disclosure, the system 10 may also be referred to as an electromechanical-positioning system. A material system 16 may be mounted to the support structure 12. The electromechanical devices 14 may include any mechanical device, electronic device, electromechanical device or combination thereof suitable to apply a force to the support structure 12 that causes a displacement in the material system 16 mounted to the support structure 12. For example, the electromechanical devices 14 may apply an electromechanical-induced force and mechanically displace at least a portion of the support structure 12 to which the material system 16 is mounted to displace the material system 16.

Thus, the disclosed system 10 may replace a thermal cycling test with an equivalent mechanical cycling test by rapidly cycling displacement and/or deformation of at least a portion of the material system 16. For example, during a testing operation, the mechanical cycling test may be performed in seconds utilizing the electromechanical devices 14 (e.g., piezoelectric transducers operating at kilohertz ("kHz") frequencies) to cycle displacement of the material system 16 in response to the electromechanical-induced force (e.g., a piezo-induced force).

The support structure 12 may include at least two material holders 18 (identified individually as material holders 18a and 18b). The material holders 18 may be spaced a distance apart from each other defining a gap 22 therebetween, such that at least one material holder 18 may be movable independently of any other material holder 18. At least a portion of the material system 16 may be securely mounted or otherwise connected (e.g., removably connected) to a mounting surface 20 of each material holder 18. The material system 16 may extend across the gap 22.

Each material holder 18 may be connected to a support base 24. In an example construction, all the material holders 18 may be connected to a single support base 24. In another example construction, each material holder 18 may be connected to its own support base 24. For example, one or more support connectors 26 may extend between the support base 24 and the material holder 18. The support base 24 may be mounted to a stationary mounting base 28. Alternatively, each material holder 18 may be mounted directly to the mounting base 28 (not shown).

At least one electromechanical device 14 (identified individually as electromechanical device 14a and 14b) may be connected to at least one of the material holders 18 to drive motion of the material holder 18 and, thus, apply the electromechanical-induced force to the material holder 18 and displace and/or deform the material system 16. For example, the electromechanical device 14 may be connected to the material holder 18 by one or more joints 30. The joint 30 may allow free movement of the material holder 18 relative to the support base 24 and/or the support connector 26. The electromechanical device 14 may move the material holder 18 in at least one direction (e.g., along an X-axis, a Y-axis and/or a Z-axis). For example, the electromechanical device 14 may provide for single-axis motion of the material holder 18 or multiple-axis motion of the material holder 18.

In an example implementation, the electromechanical device 14 may move the material holder 18 in a single direction, as indicated by directional arrow 32 (e.g., along the X-axis). In another example implementation, the electromechanical device 14 may move the material holder 18 in a single direction, as indicated by directional arrow 34 (e.g., along the Y-axis). In another example implementation, the electromechanical device 14 may move the material holder 18 in a single direction, as indicated by directional arrow 36 (e.g., along the Z-axis). In yet another example implementation, the electromechanical device 14 may move the material holder 18 in one or more multiple directions, as indicated by directional arrows 32, 34, 36 (e.g., along one or more of the X-axis, Y-axis and/or Z-axis).

In an example implementation, the electromechanical device 14 may be a piezoelectric transducer. The piezoelectric transducer may be any suitable device that deforms (e.g., bends and/or stretches) in response to an applied voltage. When the piezoelectric transducer is subjected to the applied voltage, it may deform and move the material holder 18. The deformation of the piezoelectric transducer and the displacement of the material holder 18 may be proportional to the applied voltage. Thus, the piezoelectric transducer may act as a piezoelectric actuator configured to position the material holder 18 and/or adjust the position of the material holder 18 in one or more orthogonal directions (e.g., along one or more of the X-axis, Y-axis and/or Z-axis).

The piezoelectric transducer may also act as a piezoelectric sensor configured to measure the magnitude of a force applied to the piezoelectric transducer. When the piezoelectric transducer is subjected to a stress or force, for example, as applied by the material system 16 to the material holder 18, it may generate an electrical potential or voltage proportional to the magnitude of the applied force.

In this example implementation of the electromechanical devices 14, piezoelectric transducers may operate between approximately 1 Hz and 100 kHz. In another example implementation, the piezoelectric transducers may operate between approximately 1 kHz and 100 kHz. In yet another example implementation, the piezoelectric transducers may operate between approximately 10 kHz and 50 kHz.

In another example implementation, the electromechanical device 14 may be a voice coil (e.g., including a former, a collar and a winding) and a magnet (e.g., a permanent magnet). The voice coil may provide a motive force (e.g., the electromechanical-induced force) to the material holder 18 by the reaction of a magnetic field to the current passing through it. By driving a current through the voice coil, a magnetic field may be produced. This magnetic field may cause the voice coil to react to the magnetic field from the permanent magnet, thereby moving the material holder 18 and the material system 16. For example, the voice coil may act as a linear motor, which produces a force and moves a distance.

In yet another example implementation, the electromechanical device 14 may be a motor (e.g., an electric motor). The motor may include any mechanical suitable to transfer rotary motion from the motor to a linear force (e.g., the electromechanical-induced force) to move (e.g., along one or more of the X-axis, Y-axis and/or Z-axis) the material holder 18 and the material system 16. For example, the motor may include a piston, an eccentric wheel or the like operably engaged between the motor and the material holder 18.

Other electromechanical devices 14 suitable to apply an electromechanical-induced force to the material holder 18 sufficient to displace the material system 16 are also contemplated.

Referring to FIG. 2, in one embodiment of the disclosed system 10, at least one electromechanical device 14 may be operably connected to a first material holder 18a. The opposing second material holder 18b may be stationary (e.g., rigidly connected to the support base 24). The material system 16 may be connected between the material holders 18a, 18b and may span the gap 22 defined between the material holders 18a, 18b.

A controller 38 may be electrically coupled to the electromechanical device 14. The controller 38 may provide energy to the electromechanical device 14 and may control and/or modify the amplitude and/or frequency of the electromechanical devices 14 (e.g., the electromechanical-induced force) and, thus, control the displacement and/or the orthogonal directions of movement (e.g., along the X-axis, Y-axis and/or Z-axis) of the first material holder 18a with respect to the second material holder 18a.

Referring to FIG. 3, in another embodiment of the disclosed system 10, at least one electromechanical device 14a may be operably connected to the first material holder 18a and at least one electromechanical device 14b may be operably connected to the second material holder 18b. The material system 16 may be connected between the material holders 18a, 18b and may span the gap 22 defined between the material holders 18a, 18b.

The controller 38 may be electrically coupled to the electromechanical devices 14a, 14b. The controller 38 may provide energy to the electromechanical devices 14a, 14b and may control and/or modify the amplitude and/or frequency of the electromechanical devices 14a, 14b and, thus, control the displacement and/or the orthogonal directions of movement (e.g., along the X-axis, Y-axis and/or Z-axis) of the first material holder 18a and/or the second material holder 18b, respectively.

In an example construction, a single controller 38 may communicate with the electromechanical devices 14a, 14b associated with both the first material holder 18a and the second material holder 18b. In another example construction, a discrete controller may communicate with the electromechanical devices 14a associated with the first material holder 18a and another the discrete controller (not shown) may communicate with the electromechanical devices 14b associated with the second material holder 18b.

In an example method for testing the material system 16, at various amplitudes and frequencies, the electromechanical devices 14 may displace the material holder 18 and the material system 16 (e.g., through the electromechanical-induced force) between approximately 1 micron and 200 microns. As another example, the electromechanical devices 14 may displace the material holder 18 and the material system 16 between approximately 25 microns and 100 microns. As yet another example, the electromechanical devices 14 may displace the material holder 18 and the material system 16 between approximately 25 microns and 40 microns.

Displacement of the first material holder 18a and/or the second material holder 18b with respect to each other may mechanically displace a first portion 16a of the material system 16 with respect to a second portion 16b of the material system 16 and induce stresses in the material system 16. These mechanical displacements and stresses may be substantially equivalent to thermal displacements and stresses resulting from thermal cycling, as illustrated in FIG. 1.

Referring to FIG. 4, in another embodiment of the disclosed system 10, the support structure 12 and the material system 16 may be enclosed within a testing chamber 40. The testing chamber 40 may be any sealable enclosure defining an interior volume 44 suitable to test the effects of specified environmental conditions and/or parameters on the material system 16 during the mechanical cycling test. For example, the testing chamber 40 may control various environmental testing parameters, including, but not limited to, temperature, pressure, humidity and the like.

A controller 42 may be electrically coupled to the testing chamber 40 to control the environmental conditions within the interior volume 44, receive information about the environmental conditions within the interior volume 44 and/or process the information about the environmental conditions during testing. One or more sensors 46 may be operably coupled to the interior volume 44 to monitor the environmental conditions and transmit environmental information to the controller 42. For example, the sensors 46 may include, but are not limited to, temperature sensors, pressure sensors and/or humidity sensors.

The controller 42 may include a processor 48 for processing the environmental information collected by the sensors 46. The environmental conditions within the interior volume 44 may be automatically controlled and/or changed by the processor 48 or manually controlled by an operator, for example through a user interface 50. The environmental information may be displayed to the operator, for example through the user interface 50.

A sensor 52 may be positioned to monitor the condition of the material system 16 during mechanical cycle testing. As illustrated in FIGS. 2 and 3, the sensor 52 may be positioned proximate a surface 56 of the material system 16. As illustrated in FIG. 4, the sensor 52 may be positioned within the testing chamber 40. For example, the sensor 52 may be an optical detector or a high-speed camera.

A controller 54 may be electrically coupled to the sensor 52 to control the sensor 52, receive information about the condition of the material system 16 (e.g., the surface 56 of the material system 16) and/or process the information about the condition of the material system 16 during testing (e.g., occurrence of cracking in a surface 56 of the material system 16). The controller 54 may include a processor 58 for processing the condition information (e.g., visual images) collected by the sensor 52. The condition information may be displayed to the operator, for example, by a display 60.

Figure 5:
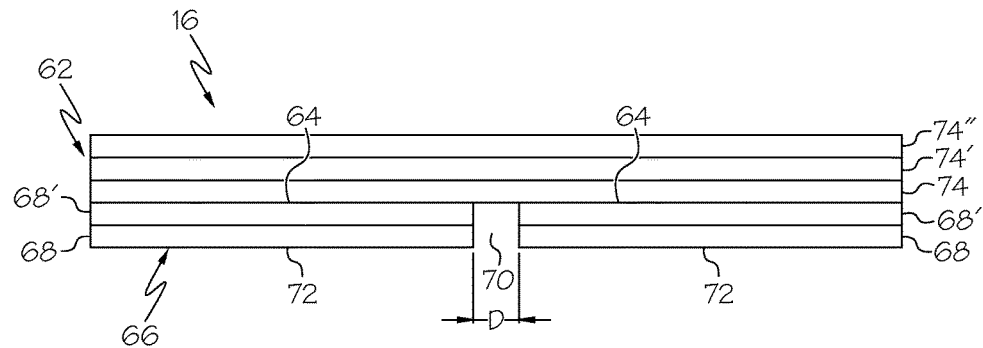
FIG. 5 is a schematic illustration of an example of the material system.
Figure 9:
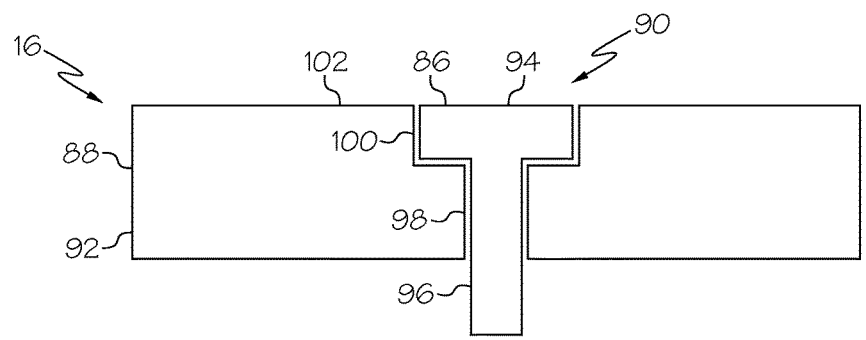
FIG. 9 is a schematic illustration of another example of the material system.

Referring to FIGS. 5 and 9, the material system 16 may include various material schemes and/or finish systems. For example, the material system 16 may include various combinations and/or configurations of materials, coatings, fasteners and the like.

Referring to FIG. 5, in an example implementation, the material system 16 may include a protective coating scheme 62 applied to a surface 64 of an underlying structure 66. The underlying structure 66 may include any of a variety of materials. For example, the underlying structure 66 may include, but is not limited to, aluminum, titanium, copper, metallic alloys, composites, fiberglass, thermoplastic (e.g., Polyether ether ketone (PEEK)) and combinations of the like. The underlying structure 66 may include a single substrate layer 68 or may include a plurality of substrate layers 68, 68' in a stacked configuration.

The protective coating scheme 62 may include any of a variety of coating materials. For example, the protective coating scheme 62 may include, but is not limited to, sealants, primers, paints and combinations of the like. The protective coating scheme 62 may include a single coating layer 74 or may include a plurality of coating layers 74, 74', 74" in a layered configuration.

In the example construction illustrated in FIG. 5, the underlying structure 66 may include two adjacent sets 72 of one or more substrate layers 68, 68' separated by a gap 70. The protective coating scheme 62 may be applied to the top surfaces 64 of each set 72 covering the gap 70. A dimension D of the gap 70 may be changed based on testing parameters. For example, the dimension D of the gap 70 may be increased or decreased based on a particular protective coating scheme 62 being tested. In another example construction (not shown), the underlying structure 66 may include a single set 72 of one or more substrate layers 68, 68' (e.g., having no gap 70). The protective coating scheme 62 may be applied to the top surface 64 of the set 72.

Figure 6:
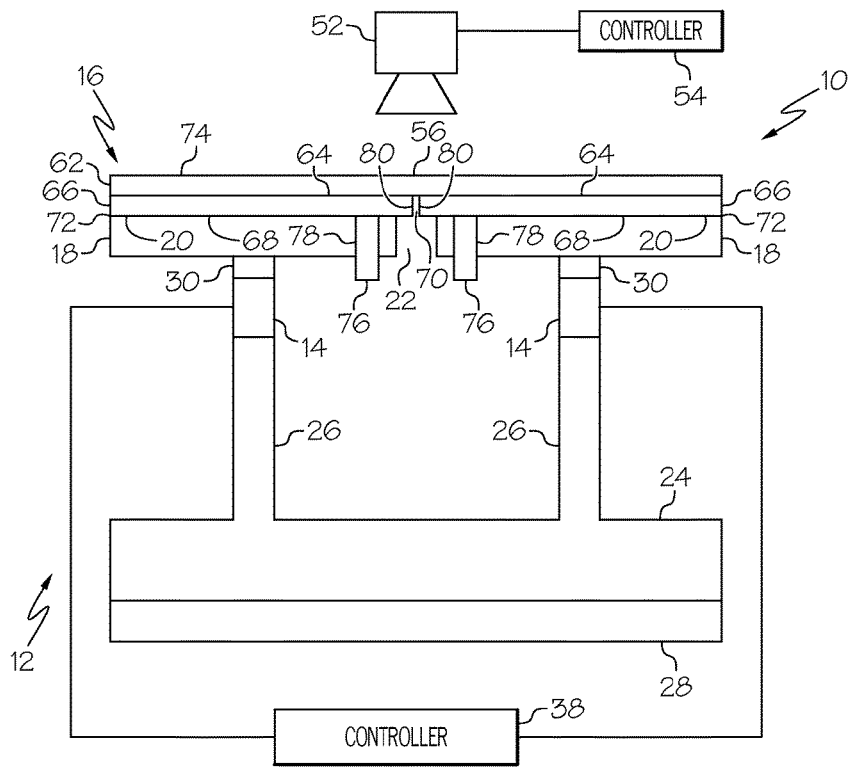
FIG. 6 is a schematic illustration of an example implementation of the disclosed system used for testing the material system of FIG. 5.

Referring to FIG. 6, in an example implementation of the disclosed system 10, the support structure 12 may be configured to mechanically test the protective coating scheme 62. The underlying structure 66 may be connected to and extend between the material holders 18 spanning the gap 22. The gap 70 disposed between the adjacent sets 72 of the substrate layer 68 may be axially aligned with gap 22 disposed between adjacent material holders 18. The dimension D (FIG. 5) of the gap 70 may be equal to or less than the dimension of the gap 22.

The underlying structure 66 may be connected to the material holders 18 in any suitable manner. In an example construction, the underlying structure 66 may include one or more posts 76 that are insertably connected within one or more through holes 78 disposed at least partially through the material holders 18. For example, each set 72 of the substrate layer 68 may include at least one post 76 extending from a surface of the substrate layer 68 opposite the surface 64 to which the protective coating scheme 62 is applied. Each material holder 18 may include at least one through hole 78 located at a position to receive a corresponding post 76 of an associated set 72 of the substrate layers 68 connected to the material holder 18.

During a mechanical testing operation of the material system 16, the electromechanical devices 14 may cycle (e.g., rapidly cycle) displacement of the material holders 18 in one or more orthogonal directions. Displacement of the material holders 18 may be transferred to the sets 72 of the substrate layer 68 and apply the electromechanical-induced force to the material system 16 to displace the substrate layers 68 about a line 82 (FIGS. 7 and 8) defined by adjacent edges 80 of the substrate layers 68 (e.g., edges 80 defining the gap 70). Displacement of the adjacent sets 72 of substrate layers 68 may induce stresses in the protective coating scheme 62 (e.g., the coating layers 74).

Figure 7:
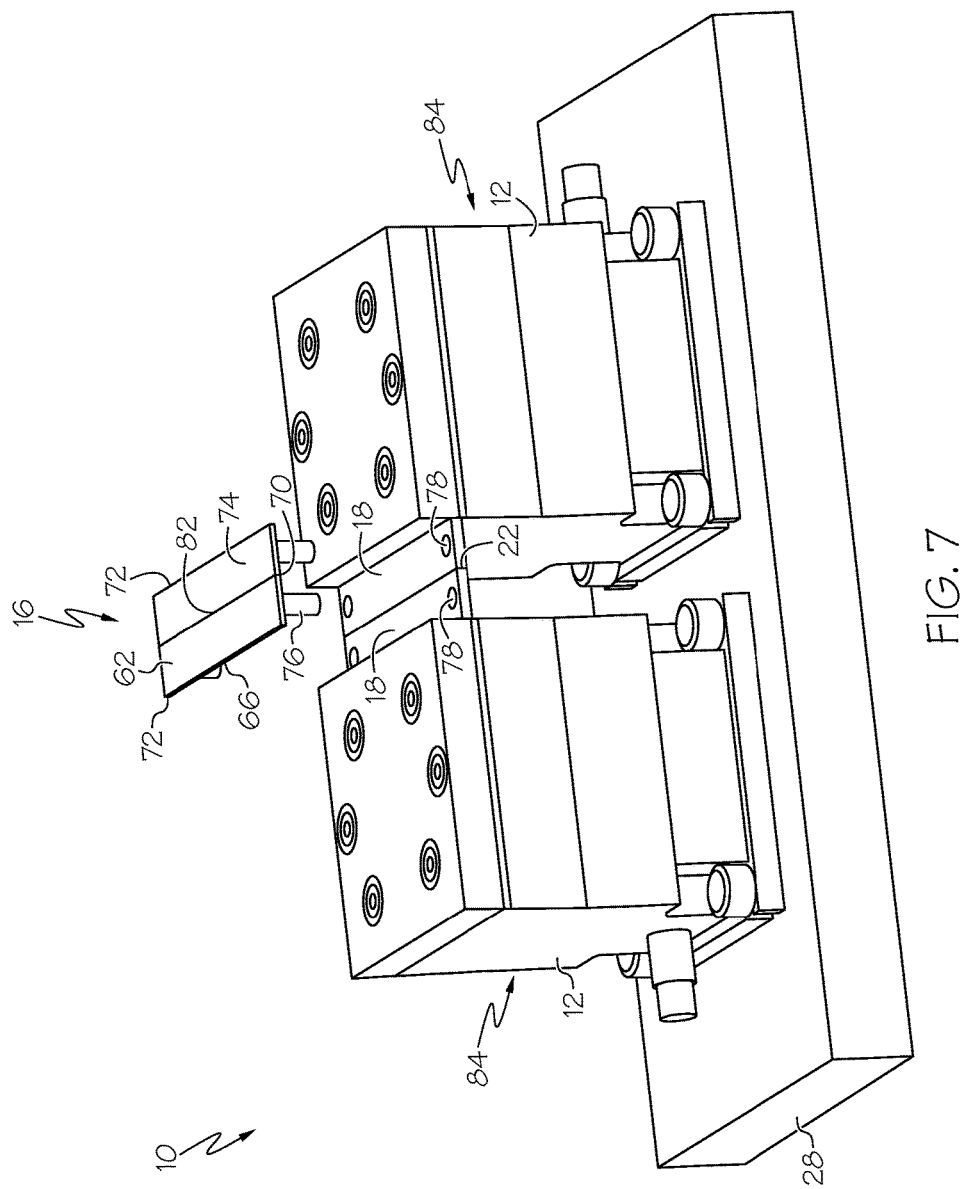
FIG. 7 is a top and front perspective view of the system of FIG. 6.
Figure 8:
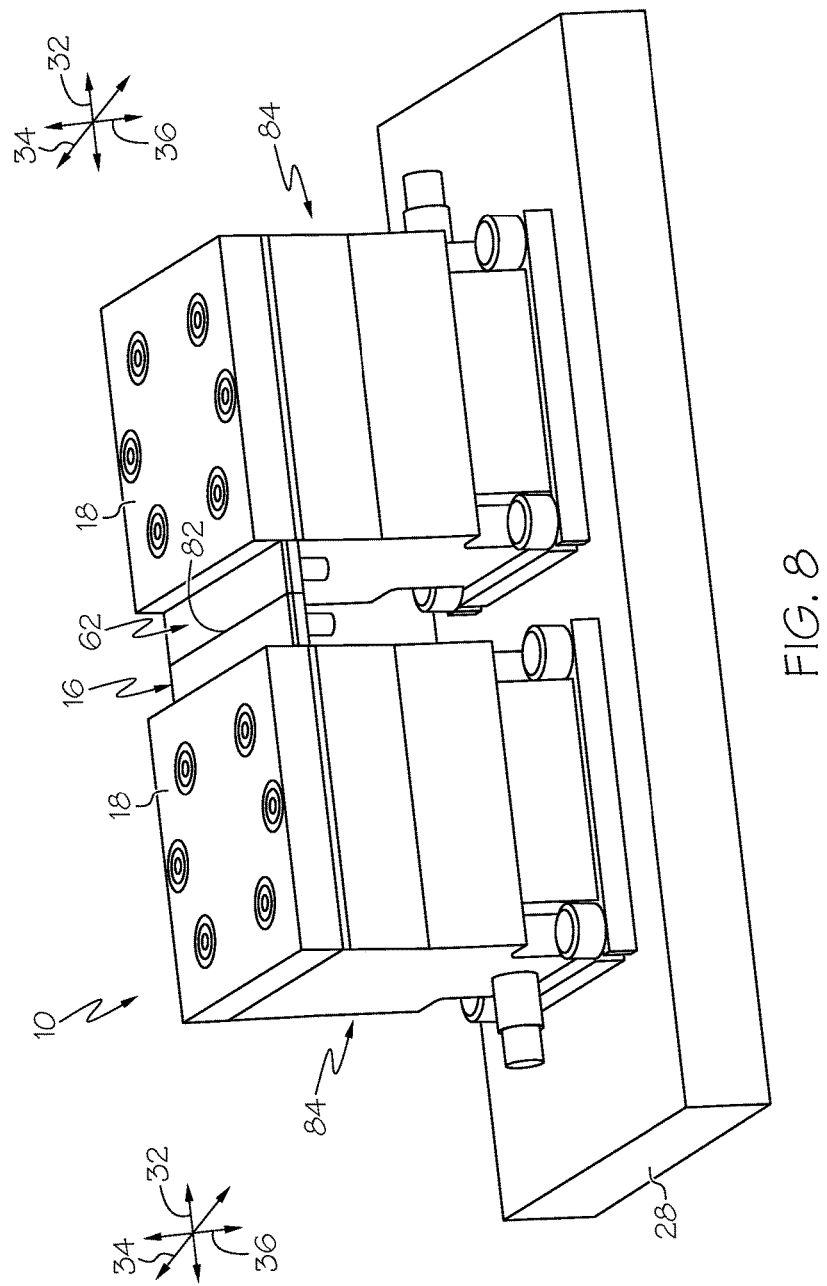
FIG. 8 is a top and front perspective view of the system of FIG. 6.

Referring to FIGS. 7 and 8, in one general, non-limiting example, the support structure 12 and electromechanical devices 14 (not shown in FIGS. 7 and 8) may be integrated into a test assembly 84. A pair of test assemblies 84 may be mounted to the mounting base 28 such that the material holders 18 of each test assembly 84 approximate each other defining the gap 22 there between. As a specific, non-limiting example, the test assemblies 84 may be commercially available single-axis or multi-axis piezo-positioning system, such as a NanoCube® XYZ Piezo Stage available from PI (Physik Instrumente) L.P. of Auburn, Mass.

As illustrated in FIGS. 7 and 8, the material system 16 (e.g., the material system 16 shown and described in FIGS. 5 and 6) may be connected to the material holders 18 of each test assembly 84, for example, through the post 76 and through hole 78 interface. Each testing assembly 84 may move the material holder 18 in one or more orthogonal directions, as indicated by directional arrows 32, 34, 36, to displace the underlying structure 66 (e.g., adjacent sets 72 of the substrate layers 68) about the gap 70 and induce stresses in the protective coating scheme 62 (e.g., the coating layers 74).

Referring to FIG. 9, in another example implementation, the material system 16 may include a fastener 86 connected to an underlying structure 88 defining a fastener interface scheme 90. The underlying structure 88 may include any of a variety of materials. For example, the underlying structure 88 may include, but is not limited to, aluminum, titanium, copper, metallic alloys, composites, fiberglass, thermoplastic (e.g., Polyether ether ketone (PEEK)) and combinations of the like. The underlying structure 88 may include a single substrate layer 92 or may include a plurality of substrate layers (not shown) in a stacked configuration.

The fastener interface scheme 90 may include any of a variety of fastener 86 and underlying structure 88 configurations. For example, the fastener 86 may include a head 94 and a shank 96. The underlying structure 88 (e.g., one or more substrate layers 92) may include a through hole 98 configured to receive the shank 96. The through hole 98 may include a counter sink 100 (or counter bore) bored into a surface 102 of the underlying structure 88 to receive the head 94. The fastener 86 (including the shank 96 and the head 94) may slide and/or otherwise move with respect to the through hole 98 and/or the countersink 100. In an example construction, the through hole 98 may be configured to receive the shank 96 (e.g., a smooth bored through hole) and a connecter (e.g., a nut) (not shown) may be connected to an end of the shank 96 protruding through the underlying structure 88.

The fastener interface scheme 90 may include a variety of characteristics including, but not limited to, the size of the fastener 86, the type of fastener 86, the material composition of the fastener 86, the material composition of the underlying structure 88, the tolerances between the through hole 98 and the shank 96, the tolerances between the counter sink 100 and the head 94 and the like.

Figure 10:
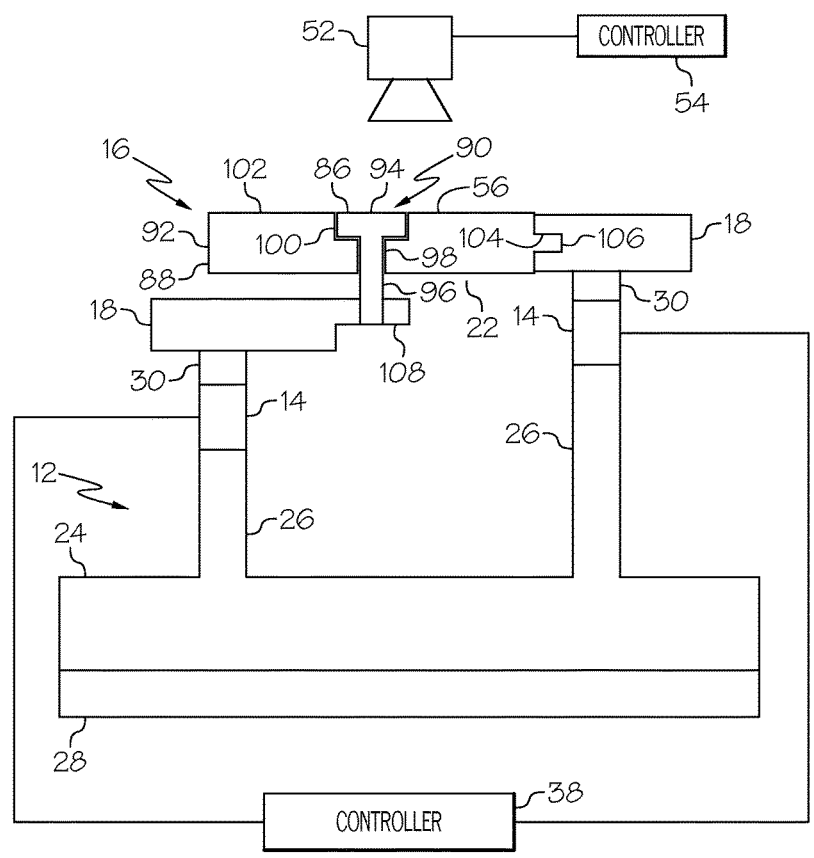
FIG. 10 is a schematic illustration of another example implementation of the disclosed system used for testing the material system of FIG. 9.

Referring to FIG. 10, in an example implementation of the disclosed system 10, the support structure 12 may be configured to mechanically test the fastener interface scheme 90. The underlying structure 88 may be connected to one of the material holders 18 and the fastener 86 may be connected to another one of the material holders 18 such that the underlying structure 88 and the fastener 86 extend between the material holders 18 spanning the gap 22.

The underlying structure 88 and the fastener 86 may be connected to the material holders 18 in any suitable manner. In an example construction, the underlying structure 88 may include one or more posts 104 that are insertably connected within one or more slots 106 disposed at least partially through an associated material holder 18. The opposing material holder 18 may include a clamp 108 configured to engage at least a portion of the shank 96 protruding through the underlying structure 88. For example, the clamp 108 may be an adjustable clamping mechanism configured to grip the shank 96. As another example, the clamp 108 may include a through hole configured to engageably mate with the shank 96.

During a mechanical testing operation of the material system 16, the electromechanical devices 14 may cycle (e.g., rapidly cycle) displacement of the material holders 18 in one or more orthogonal directions. Displacement of the material holders 18 may be transferred to the one or both of the underlying structure 88 (e.g., the substrate layer 92) and/or the fastener 86 and displace the underlying structure 88 and the fastener 86 with respect to one another about the through hole 98 and the counter sink 100. Displacement of the underlying structure 88 and the fastener 86 with respect to one another may induce stresses in the fastener interface scheme 90 (e.g., between the fastener 86 and the underlying structure 88).

Figure 11:
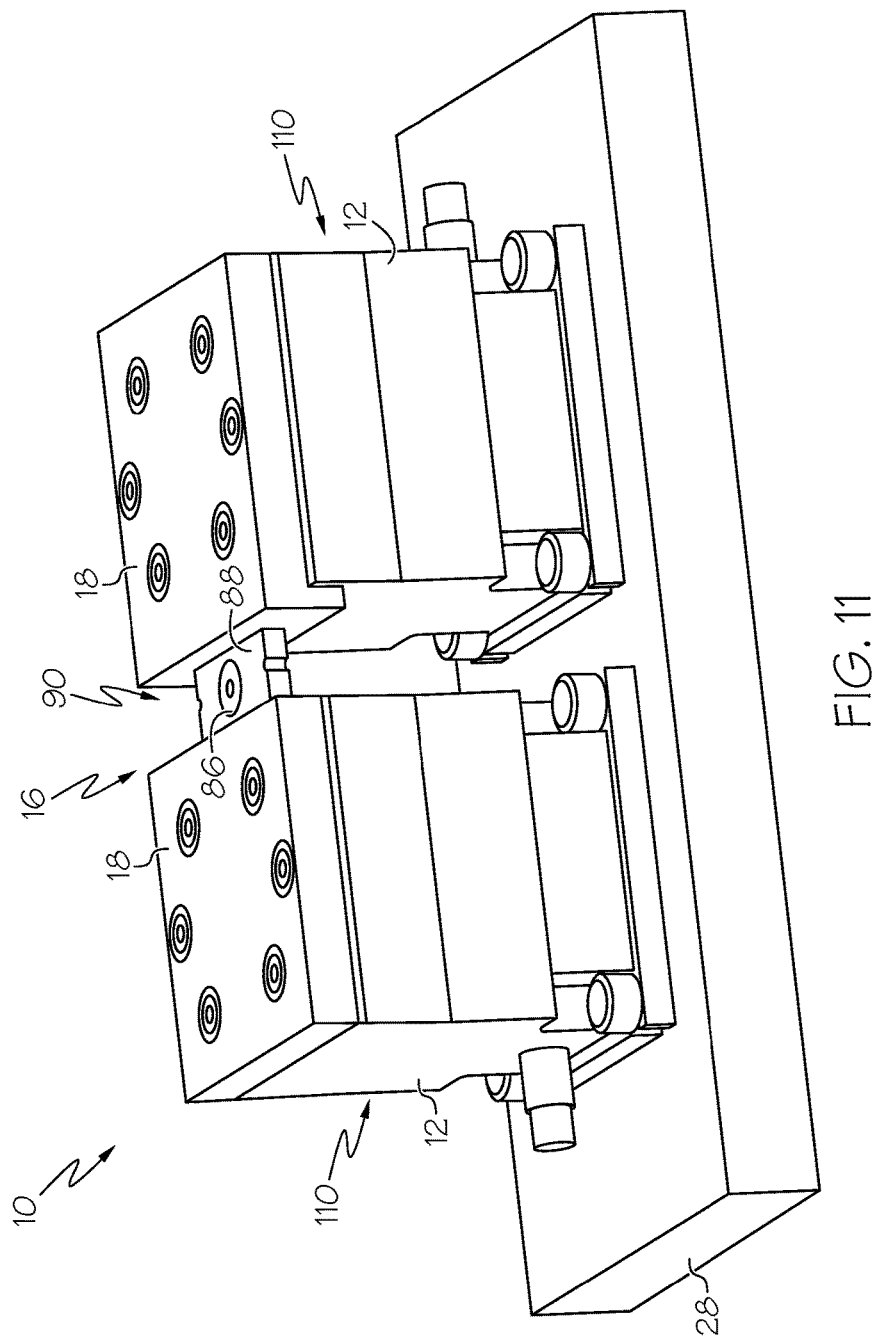
FIG. 11 is a top and front perspective view of the system of FIG. 10.
Figure 12:
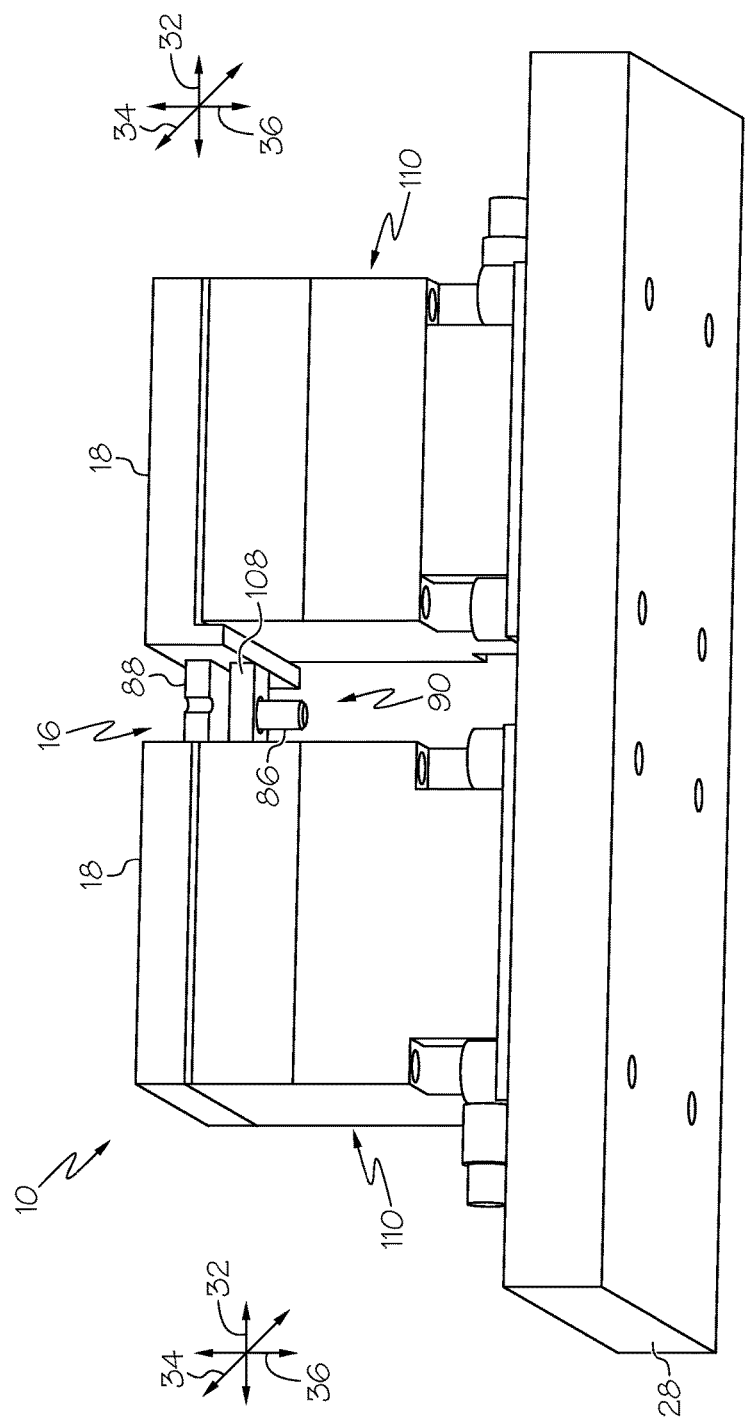
FIG. 12 is a bottom and front perspective view of the system of FIG. 10.

Referring to FIGS. 11 and 12, in one general, non-limiting example, the support structure 12 and electromechanical devices 14 (not shown in FIGS. 11 and 12) may be integrated into a test assembly 110. A pair of test assemblies 110 may be mounted to the mounting base 28 such that the material holders 18 of each test assembly 110 are suitably positioned to retain the underlying structure 88 and the fastener 86. As a specific, non-limiting example, the test assemblies 110 may be commercially available single-axis or multi-axis piezo-positioning system, such as a NanoCube® XYZ Piezo Stage available from PI (Physik Instrumente) L.P. of Auburn, Mass.

As illustrated in FIGS. 11 and 12, the material system 16 (e.g., the material system 16 shown and described in FIGS. 9 and 10) may be connected to the material holders 18 of each test assembly 110. For example, the post 104 may connect within the slot 106 (FIG. 10) of the material holder 18 of one test assembly 110 and the clamp 108 of the material holder 18 of an opposing test assembly 110 may connect to the fastener 86. Each testing assembly 84 may move the material holder 18 in one or more orthogonal directions, as indicated by directional arrows 32, 34, 36, to displace the underlying structure 88 (e.g., substrate layer 92)

and the fastener 86 with respect to one another and induce stresses in the fastener interface scheme 90.

Figure 13:
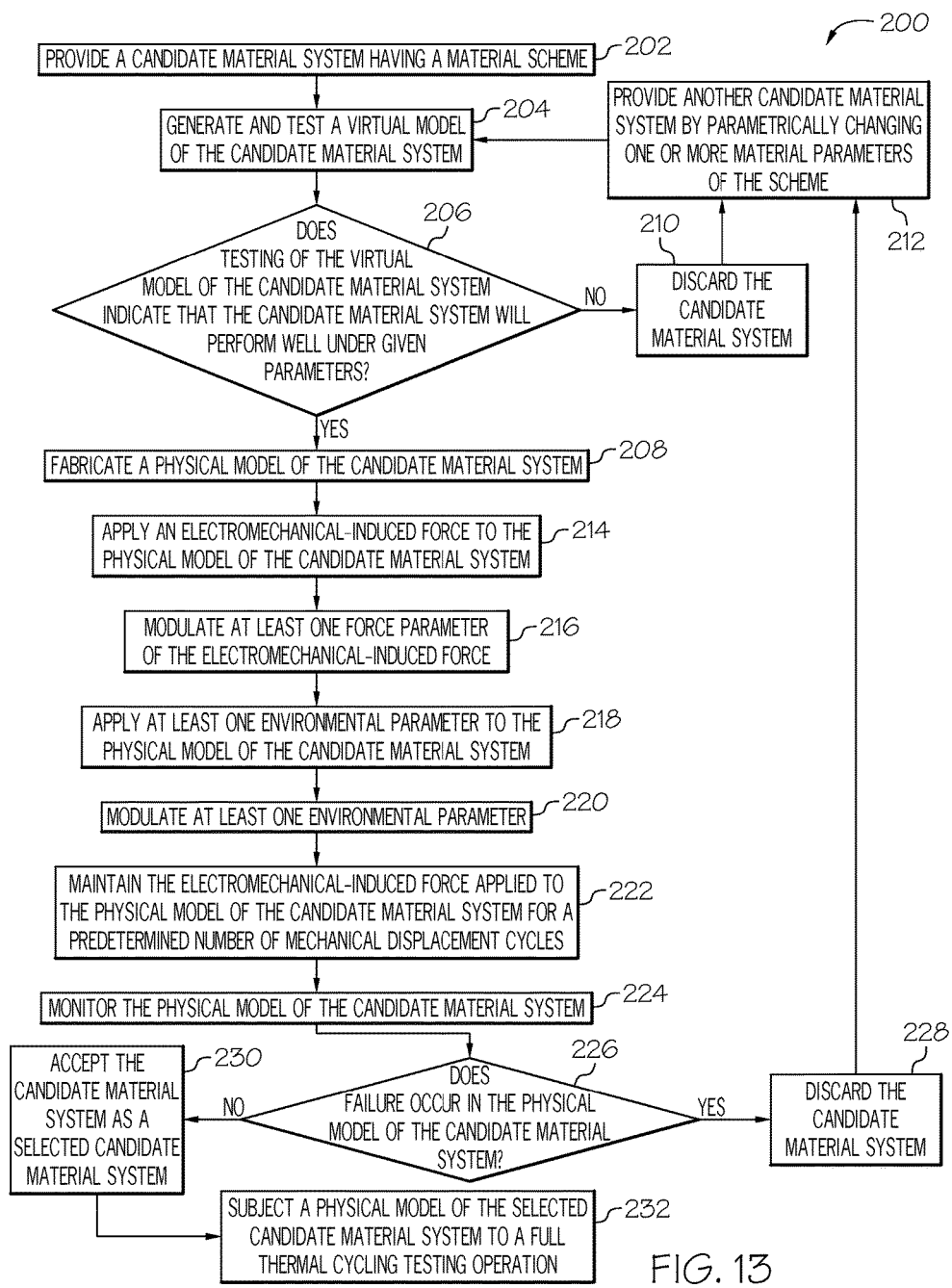
FIG. 13 is a flow diagram of one embodiment of the disclosed method for testing a material.

Referring to FIG. 13, one embodiment of the disclosed method, generally designated 200, for testing a material system may begin at block 202 by providing one or more candidate material systems. For example, the candidate material system may include the material system 16 shown and described in FIG. 5 or the material system 16 shown and described in FIG. 9.

The candidate material system may be developed by setting up a scheme of materials (e.g., the protective coating scheme 62 shown and described in FIG. 5 or the fastener interface scheme 90 shown and described in FIG. 9). The scheme may include various material parameters including, but not limited to, geometry, material composition, dimensions (e.g., thicknesses), thermal capacity, heat capacity, density, coefficient of thermal expansion, thermal conductivity, Young's modulus, Poisson's ratio and the like of each of the materials included in the scheme.

As shown at block 204, a virtual model of the candidate material system may be generated and tested to test the response to various conditions (e.g., dynamic forces and/or environmental conditions) on the candidate material system. For example, the candidate material system may be thermally modeled and/or mechanically modeled, such as with a Finite Element Analysis software tool.

As shown at block 206, if virtual testing of the virtual model of the candidate material system indicates that the candidate material system will perform well (e.g., stresses induced by thermal and/or mechanical displacements do not lead to failure of the candidate material system) under the given testing parameters (e.g., under conditions similar to which a material system will be subjected to during operation), then a physical model of the candidate material system may be fabricated, as shown at block 208. If virtual testing of the virtual model of the candidate material system indicates that the candidate material system will not perform well (e.g., stresses induced by thermal and/or mechanical displacements lead to failure of the candidate material system) under the given testing parameters, then the candidate material system may be discarded, as shown at block 210, and another candidate material system may be provided by parametrically changing one or more of the material parameters of the scheme, as shown at block 212.

Subsequent candidate material systems having different scheme parameters may proceed through the method steps shown at blocks 204 and 206 until a candidate material system is accepted.

As shown at block 208, a physical model of the candidate material system may be fabricated. As shown at block 214, an electromechanical-induced force (e.g., a dynamic force) may be applied to the physical model of the candidate material system. For example, the physical model of the candidate material system may be tested using a single-axis or a multi-axis electromechanical-positioning system (e.g., a piezo-positioning system, a voice coil-positioning system, a motor-positioning system or the like), such as the system 10 shown and described in FIGS. 2-12. The electromechanical-positioning system may mechanically cycle displacement of least a portion of the physical model of the candidate material system with respect to another portion of the physical model of the candidate material system. For example, the electromechanical-positioning system may apply the electromechanical-induced force (e.g., a piezo-induced force) in a sinusoidal manner or by an arbitrary waveform structure.

As shown at block 216, at least one force parameter of the electromechanical-induced force may be modulated and/or changed. For example, displacement amplitude, phase, frequency, gap expansion (e.g., gap 22 and/or gap 70), multi-axial orthogonal displacements and other variables may be parametrically changed throughout the mechanical cycling of the physical model of the candidate material system.

As shown at block 218, at least one environmental parameter (e.g., temperature, pressure and/or humidity) may be applied to the candidate material system. For example, the electromechanical-positioning system and the physical model of the candidate material system may be mechanically tested within a testing chamber, such as the testing chamber shown and described in FIG. 4.

As shown at block 220, one or more environmental parameter (e.g., temperature, pressure and/or humidity) may be modulated and/or changed throughout the mechanical cycling of the physical model of the candidate material system.

As shown at block 222, the electromechanical-induced force applied to the physical model of the candidate material system may be maintained to displace the physical model of the candidate material system. For example, the electromechanical-induced force may be maintained for a predetermined number of mechanical displacement cycles (e.g., a test block). As another example, the electromechanical-induced force may be maintained until failure occurs (e.g., cracking) in the material system. Force parameters and/or environmental parameters may be modulated and/or changed throughout the test block, as shown at blocks 216 and 212.

As shown at block 224, the physical model of the candidate material system may be monitored throughout the predetermined number of mechanical displacement cycles. For example, the physical model of the candidate material system may be monitored by one or more sensors, such as the sensor 52 shown and described in FIGS. 2-4.

Failure (e.g., cracks) may form from maintaining, modulating and/or changing the force parameters and/or the environmental parameters and subjecting the physical model of the candidate material to constant and/or varying motion in response to the electromechanical-induced force.

As shown at block 226, if a failure occurs (e.g., cracking) in the physical model of the candidate system, for example, during the predetermined number of mechanical displacement cycles, then the candidate material system may be discarded (e.g., an unselected candidate material system), as shown at block 228, and another candidate material system may be provided by parametrically changing one or more of the material parameters of the scheme, as shown at block 212.

Subsequent candidate material systems having different scheme parameters may proceed through the method steps shown at blocks 204 and 226 until a candidate material system is accepted.

As shown at block 230, if a failure does not occur in the physical model of the candidate material system during the predetermined number of mechanical displacement cycles, then the candidate material system may be accepted as a selected candidate material system.

As shown at block 232, a physical model of the selected material candidate system may be subjected to a full thermal cycling testing operation.

Thus, the disclosed method 200 may significantly speed the evaluation of material performance (e.g., via crack propagation) of a candidate material system prior to conducting a full thermal cycling testing operation on the candidate material system.

Accordingly, the disclosed system 10 and method 200 for material testing may replace thermal expansion with mechanically driven displacements using electromechanical devices (e.g., piezoelectric transducers, voice coils, motors or the like) that can be cycled at rapid rates (e.g., kHz rates). Thus, a test block (e.g., a number of deformation cycles) may be achieved in fractions of a second as opposed to many days using a thermal cycling method.

Figure 14:
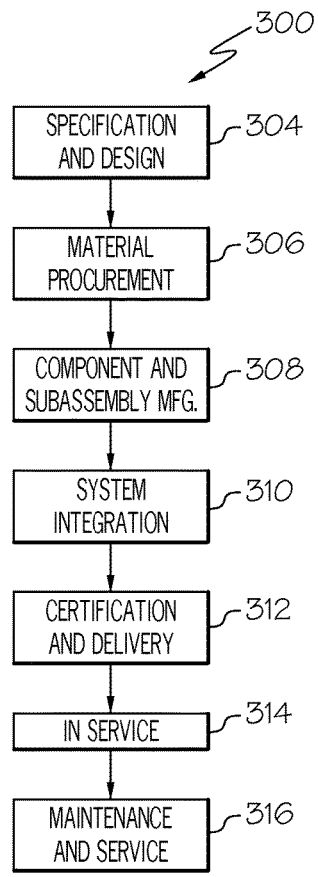
FIG. 14 is flow diagram of an aircraft production and service methodology.
Figure 15:
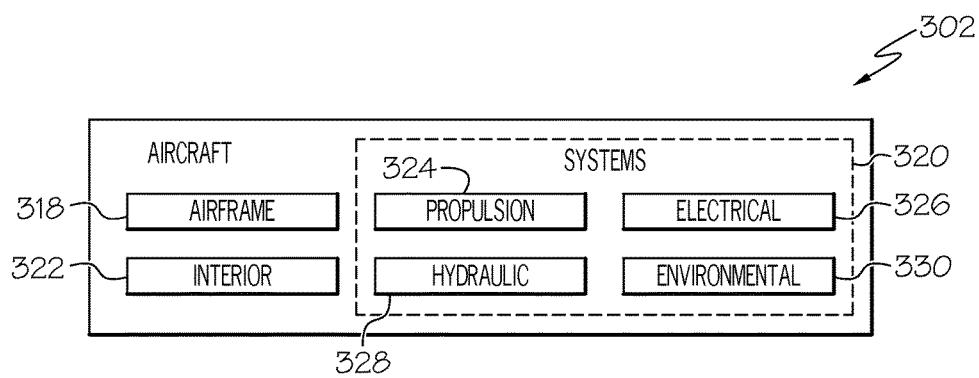
FIG. 15 is a block diagram of an aircraft.

Examples of the disclosure may be described in the context of an aircraft manufacturing and service method 300, as shown in FIG. 14, and an aircraft 302, as shown in FIG. 15. During pre-production, the aircraft manufacturing and service method 300 may include specification and design 304 of the aircraft 302 and material procurement 306. During production, component/subassembly manufacturing 308 and system integration 310 of the aircraft 302 takes place. Thereafter, the aircraft 302 may go through certification and delivery 312 in order to be placed in service 314. While in service by a customer, the aircraft 302 is scheduled for routine maintenance and service 316, which may also include modification, reconfiguration, refurbishment and the like.

Each of the processes of method 300 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 15, the aircraft 302 produced by example method 300 may include an airframe 318 with a plurality of systems 320 and an interior 322. Examples of the plurality of systems 320 may include one or more of a propulsion system 324, an electrical system 326, a hydraulic system 328, and an environmental system 330. Any number of other systems may be included. Although an aerospace example is shown, the principles of the disclosed system 10 and method 200 may be applied to other industries, such as the automotive, petroleum or any other industry requiring operations at extreme environments.

Apparatus and methods embodied herein may be employed during any one or more of the stages of the production and service method 300. For example, components or subassemblies corresponding to component/subassembly manufacturing 308, system integration 310, and or maintenance and service 316 may be fabricated or manufactured using the disclosed system 10 (FIGS. 2-12) and method 200 (FIG. 13). Also, one or more apparatus examples, method examples, or a combination thereof may be utilized during component/subassembly manufacturing 308 and/or system integration 310, for example, by substantially expediting assembly of or reducing the cost of an aircraft 302, such as the airframe 318 and/or the interior 322. Similarly, one or more of apparatus examples, method examples, or a combination thereof may be utilized while the aircraft 302 is in service, for example and without limitation, to maintenance and service 316.

Although various embodiments of the disclosed system and method have been shown and described, modifications may occur to those skilled in the art upon reading the specification. The present application includes such modifications and is limited only by the scope of the claims.

What is claimed is:

1. A system for testing a multicomponent material system, said system comprising:
   a first material holder to hold a first underlying structure of said multicomponent material system, said first underlying structure comprising a first surface and a first edge; and
   a second material holder to hold a second underlying structure of said multicomponent material system, said second underlying structure being separate from said first underlying structure and comprising a second surface and a second edge, such that said first surface and said second surface share a common virtual plane and said first edge and said second edge abut each other to form an edgewise interface that is perpendicular to said common virtual plane;
   a first piezoelectric transducer operably connected to said first material holder to apply a first electromechanical-induced force to said first material holder that reciprocally moves said first material holder relative to said second material holder in at least one axial direction; and
   a second piezoelectric transducer operably connected said second material holder to apply a second electromechanical-induced force to said second material holder and reciprocally move said second material holder relative to said first material holder in at least one axial direction; and wherein:
   linear movement of said first material holder relative to said second material holder causes a mechanical displacement between said first underlying structure and said second underlying structure along said edgewise interface and orthogonal to said common virtual plane and induces a mechanical stress in a coating layer of said multicomponent material system that covers said first surface and said second surface over said edgewise interface and that shares said common virtual plane,
   operating frequencies of said first piezoelectric transducer and said second piezoelectric transducer are selected between approximately 1 Hz and approximately 100 kHz so that said mechanical displacement between said first underlying structure and said second underlying structure along said edgewise interface is substantially equivalent to a predefined thermal displacement between said first underlying structure and said second underlying structure along said edgewise interface caused by thermal expansion, and
   said mechanical stress induced in said coating layer by said mechanical displacement simulates a thermal stress induced in said coating layer by said thermal displacement.

2. The system of claim 1 wherein:
   said mechanical displacement is less than approximately 200 microns.

3. The system of claim 1 further comprising:
   a sensor for collecting information about a condition of said coating layer;
   a processor for analyzing said information about said condition of said coating layer; and
   a controller in communication with said piezoelectric transducer, wherein said controller controls at least one force parameter of said electromechanical-induced force to mechanically simulate a thermal displacement cycle.

4. The system of claim 3 further comprising:
   a sealable testing chamber, wherein said sealable testing chamber controls at least one environmental parameter, wherein said material system is located within said testing chamber; and
   a second sensor to collect information about an environmental condition within said testing chamber, wherein said processor analyzes said information about said environmental condition within said testing chamber.

5. The system of claim 1 wherein:
   said first material holder and said second material holder are spaced apart defining a gap therebetween, and
   said edgewise interface is substantially aligned with said gap.

6. The system of claim 1 wherein:
   said first material holder comprises a flat first mounting surface and a first mounting edge,
   said second material holder comprises a flat second mounting surface and a second mounting edge,
   said first mounting surface and said second mounting surface are in a coplanar relationship,
   said first mounting edge and said second mounting edge are in edgewise alignment with one another,
   said first mounting surface is configured to engage and support said first underlying structure,
   said second mounting surface is configured to engage and support said second underlying structure, and
   said first material holder and said second material holder maintain a coplanar relationship between said first surface said first underlying structure and said second surface of said second underlying structure and maintain an abutting relationship between said first edge and said second edge along said edgewise interface until application of said electromechanical-induced force.

7. The system of claim 6 wherein:
   said first mounting edge and said second mounting edge are spaced apart defining a gap therebetween, and
   said edgewise interface formed by said first edge and said second edge is substantially aligned with said gap.

8. The system of claim 6 wherein:
   said first material holder further comprises at least one first mounting hole extending through said first mounting surface and configured to receive and retain at least one first post depending from said first underlying structure, and
   said second material holder further comprises at least one second mounting hole extending through said second mounting surface and configured to receive and retain at least one second post depending from said second underlying structure.

9. The system of claim 1 wherein:
   said first material holder and said second material holder are offset from one another,
   said first material holder comprises a slot configured to receive and retain a post depending outwardly from said first underlying structure,
   said second material holder comprises a clamp configured to engage and retain said second underlying structure, and
   said first material holder and said second material holder maintain a coplanar relationship between said first surface of said first underlying structure and said second surface of said second underlying structure and maintain an abutting relationship between said first edge and said second edge along said edgewise interface until application of said electromechanical-induced force.

10. The system of claim 1 further comprising:
a base;
a first support extending from said base;
a first joint movably coupling said first material holder with said first support so that said first material holder is freely movable along three axial directions in response to said first electromechanical-induced force applied to said first material holder by said first piezoelectric transducer;
a second support extending from said base; and
a second joint movably coupling said second material holder with said second support so that said second material holder is freely movable along three axial directions in response to said second electromechanical-induced force applied to said second material holder by said second piezoelectric transducer.

11. A method for testing a multicomponent material system, said method comprising:
utilizing said multicomponent material system comprising:
a first underlying structure comprising a first surface and a first edge;
a second underlying structure separate from said first underlying structure and comprising a second surface and a second edge, said first surface and said second surface share a common virtual plane and said first edge and said second edge abut each other to form an edgewise interface that is perpendicular to said common virtual plane; and
a coating layer that covers at least a portion of said first surface and said second surface over said edgewise interface and that shares said common virtual plane;
determining a mechanical displacement between said first underlying structure and said second underlying structure along said edgewise interface that is substantially equivalent to a predefined thermal displacement between said first underlying structure and said second underlying structure along said edgewise interface resulting from thermal expansion in at least one of said first underlying structure and said second underlying structure;
coupling said first underlying structure to a first material holder in a first position;
coupling said second underlying structure to a second material holder in a second position;
applying, by a first piezoelectric transducer operatively coupled said first material holder, a first electromechanical-induced force to said first material holder to reciprocally move said first material holder relative to said second material holder in at least one axial direction;
applying, by a second piezoelectric transducer operatively coupled said second material holder, a second electromechanical-induced force to said second material holder to reciprocally move said second material holder relative to said first material holder in at least one axial direction;
selecting an operating frequency of each one of said first piezoelectric transducer and said second piezoelectric transducer between approximately 1 Hz and approximately 100 kHz to achieve said mechanical displacement;
causing said mechanical displacement between said first underlying structure and said second underlying structure along said edgewise interface and orthogonal to said common virtual plane in response to reciprocal movement of said first material holder and said second material holder with respect to one another;
inducing a mechanical stress in said coating layer by said mechanical displacement that simulates a thermal stress induced in said coating layer by said thermal displacement; and
cycling said mechanical displacement to mechanically simulate a thermal displacement cycle.

12. The method of claim 11 wherein said cycling step comprises modulating at least one force parameter of at least one of said first electromechanical-induced force and said second electromechanical-induced force.

13. The method of claim 11 further comprising applying at least one environmental parameter to said material system.

14. The method of claim 11 further comprising monitoring a condition of said material system through said cycling step.

15. The method of claim 11 wherein said cycling step comprises applying and ceasing at least one of said first electromechanical-induced force and said second electromechanical-induced force for a predetermined number of mechanical displacement cycles substantially equivalent to a predetermined number of thermal displacement cycles.

16. The method of claim 11 wherein said cycling step comprises applying and ceasing at least one of said first electromechanical-induced force and said second electromechanical-induced force until a crack occurs in said coating layer.

17. The method of claim 11 wherein said material system further comprises a plurality of coating layers applied to said first surface and said second surface and extending across said edgewise interface.

18. The method of claim 11 wherein:
said first underlying structure comprises a first substrate comprising said first surface and said first edge,
said second underlying structure comprises a second substrate comprising said second surface and said second edge, and
said first edge and said second edge are linear and said edgewise interface formed by said first edge and said second edge is linear.

19. The method of claim 11 wherein:
said first underlying structure comprises a first substrate comprising said first surface and said first edge,
said second underlying structure comprises a second substrate comprising said second surface and said second edge,
said first edge and said second edge are nonlinear and said edgewise interface formed by said first edge and said second edge is nonlinear.

20. The method of claim 11 wherein:
said first underlying structure comprises a first substrate comprising said first surface and a through hole forming said first edge,
said second underlying structure comprises a fastener comprising said second surface and said second edge,
said first edge and said second edge are nonlinear and said edgewise interface formed by said first edge and said second edge is nonlinear.

21. The method of claim 11 wherein said coating layer comprises a protective coating that is applied to said first surface and said second surface and extends across said edgewise interface formed by said first edge and said second edge.

* * * * *